(12) United States Patent
Johnson

(10) Patent No.: US 8,482,305 B2
(45) Date of Patent: Jul. 9, 2013

(54) MECHANISMS FOR DETECTING EXPOSURE TO WATER IN AN ELECTRONIC DEVICE

(75) Inventor: Timothy M. Johnson, San Jose, CA (US)

(73) Assignee: Apple Inc., Cupertino, CA (US)

( * ) Notice: Subject to any disclaimer, the term of this patent is extended or adjusted under 35 U.S.C. 154(b) by 330 days.

(21) Appl. No.: 12/854,712

(22) Filed: Aug. 11, 2010

(65) Prior Publication Data
US 2012/0038374 A1 Feb. 16, 2012

(51) Int. Cl.
*G01R 27/08* (2006.01)
(52) U.S. Cl.
USPC ......................................... 324/694
(58) Field of Classification Search
USPC ......................................... 324/694
See application file for complete search history.

(56) References Cited

U.S. PATENT DOCUMENTS

| | | | | |
|---|---|---|---|---|
| 3,847,547 A * | 11/1974 | Delgendre et al. | .............. | 436/73 |
| 4,506,540 A * | 3/1985 | Marsh | ........................... | 73/29.05 |
| 4,942,364 A | 7/1990 | Nishijima et al. | | |
| 5,537,095 A * | 7/1996 | Dick et al. | ................. | 340/573.5 |
| 5,606,264 A * | 2/1997 | Licari et al. | ................ | 324/755.1 |
| 5,795,942 A | 8/1998 | Rhee et al. | | |
| 6,603,319 B1 | 8/2003 | Kasahara et al. | | |
| 6,683,535 B1 | 1/2004 | Utke | | |
| 6,870,986 B1 * | 3/2005 | Stone | ................ | 385/17 |
| 7,439,750 B2 * | 10/2008 | Lindorfer | ...................... | 324/696 |
| 2005/0251300 A1 * | 11/2005 | Hellvik | ........................... | 701/21 |
| 2006/0032761 A1 | 2/2006 | Oguri | | |
| 2007/0259469 A1 * | 11/2007 | Santagato | ........................ | 438/49 |
| 2009/0206853 A1 * | 8/2009 | Hawkins | ........................ | 324/696 |
| 2011/0109333 A1 * | 5/2011 | Porjo et al. | ..................... | 324/694 |

FOREIGN PATENT DOCUMENTS

WO WO 2009115131 * 9/2009
WO WO-2009115131 A1 9/2009

* cited by examiner

*Primary Examiner* — Jeff Natalini
(74) *Attorney, Agent, or Firm* — Womble Carlyle Sandridge & Rice LLP

(57) ABSTRACT

A component carrier has formed therein a water sensor, having a first patterned conductor piece formed in a metal layer of the component carrier and a bridge being an amount of water-soluble conductive glue filling an electrically insulating gap between the patterned conductor piece and another conductor in the carrier. This forms a conductive path between the patterned conductor piece and the another conductor. A sensing circuit is coupled to detect changes in impedance of the path. In another embodiment, a discrete component has a pair of terminals with a bridge being an amount of water-soluble conductive glue filling the electrically insulating gap between the terminals to form a conductive path whose impedance changes in response to coming into contact with a sufficient amount of water. Other embodiments are also described and claimed.

20 Claims, 9 Drawing Sheets

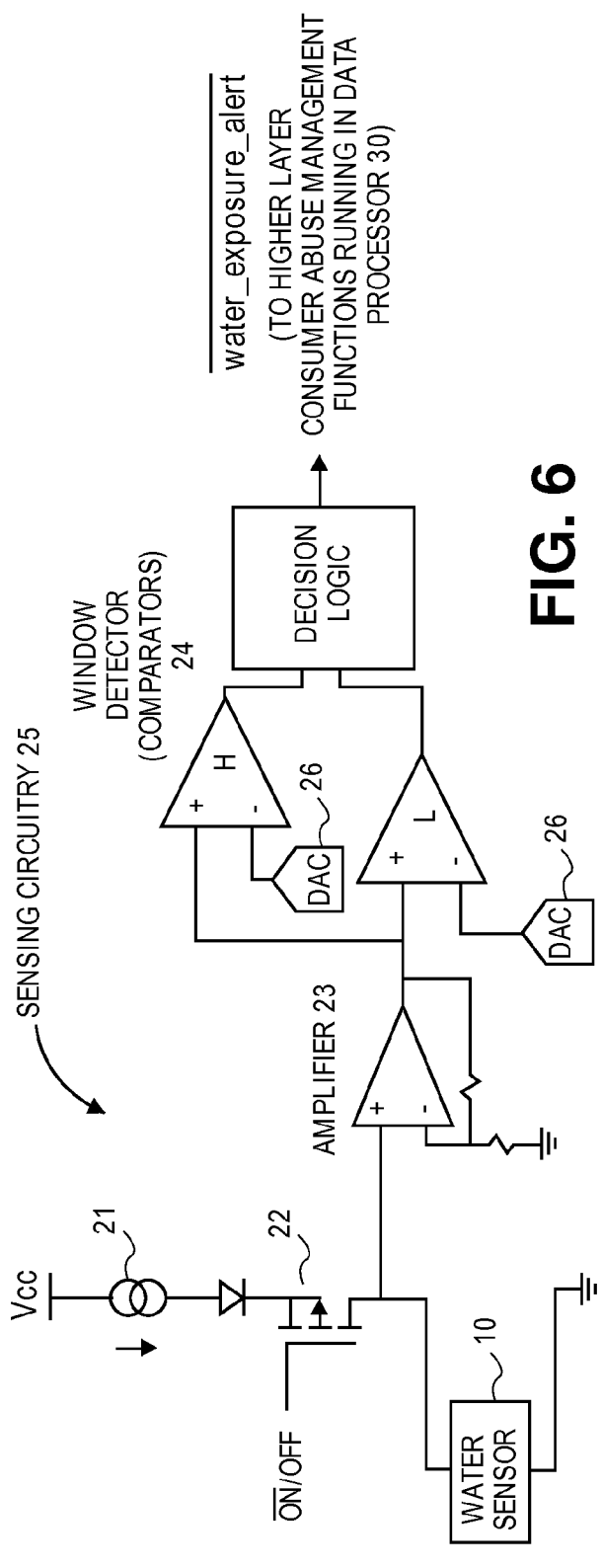
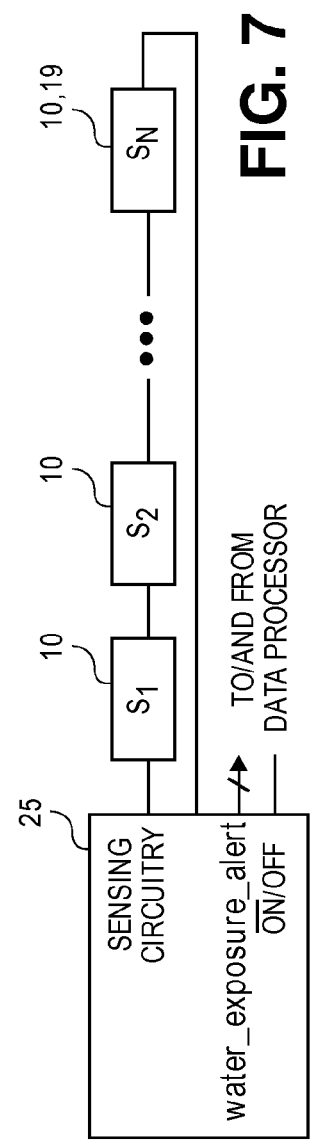
FIG. 6
FIG. 7

MECHANISMS FOR DETECTING EXPOSURE TO WATER IN AN ELECTRONIC DEVICE

BACKGROUND

The present invention relates generally to electronic devices and, more particularly, to techniques for detecting unwanted water intrusion in consumer electronic devices.

RELATED ART

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Electronic products purchased by consumers are usually sold with a warranty or return policy accompanying the product in which the vendor and/or manufacturer warrants that the product is free from defects and will remain operable for at least a limited period of time. For example, typical warranty and return policies may specify that in the event a defect is discovered in a product, or that the product becomes inoperable during the warranty period, the manufacturer or vendor will either replace the product or provide repair services to restore the product to an operational state at little or no additional charge to the consumer.

In general, such warranty and return policies are intended only to cover failures and defects relating to the manufacture or design of the product, and typically do not cover product failure that occurs as the result of consumer abuse. In fact, many warranty policies explicitly exclude returns or repair when damage from consumer abuse, whether intentional or unintentional, is the underlying cause of the product failure. For example, consumer abuse may include exposing an electronic device to unwanted conductive liquids, such as water, extreme temperatures, or excessive shock (e.g., the resulting impact from dropping the device).

Inevitably, a percentage of products sold will eventually malfunction or become inoperable at some point during the product's lifetime. When this occurs, and if the product is still within the warranty period, the purchasing consumer may elect to return the failing or inoperable device to the vendor at the point of sale or directly to the manufacturer for either service or replacement in accordance with the terms of the warranty agreement.

However, a problem arises when a device has failed due to consumer abuse, which may not be readily apparent upon a cursory inspection, but a consumer attempts to return the device for repair or replacement under the warranty. Often, particularly at a point of sale, personnel receiving the returned device may be unqualified or untrained to determine whether or not a device has failed due to manufacturing defects or due to consumer abuse. Thus, personnel at the point of sale may often times exchange the returned product with a working replacement product regardless of the cause of failure in order to avoid potential conflicts with the customer. As a result, it is not uncommon for consumers to receive replacement products or repair services on abused products not covered under the terms of a warranty. Such erroneous replacements or repairs may be costly to the vendor and/or manufacturer of the product.

SUMMARY

It would be desirable to detect consumer abuse without having to rely upon the statements of the user who may be returning a unit that is no longer working according to the original specification of the manufacturer. An embodiment of the invention is a water sensor mechanism, which may be used to automatically detect unwanted exposure of a printed wiring board (PWB) or printed circuit board (PCB) in the electronic device, to an amount of water that is likely to cause a malfunction or damage to sensitive electronic components. This water immersion detection mechanism could replace a typical solution in which a pair of bare or exposed sensor electrodes are monitored for a "short" that is caused by water electrically connecting the two electrodes. Several embodiments of the invention are now described.

In one embodiment, a component carrier (such as a rigid PWB or a flex circuit) has formed therein a first water sensor, where the sensor is composed of a first patterned conductor piece formed in a metal layer of the carrier and a bridge being an amount of water-soluble conductive glue that fills an electrically insulating gap between the patterned conductor piece and another conductor in the carrier; this forms a conductive path that connects the two conductors. A sensing circuit (also integrated in the electronic device) is coupled to the two conductors to detect changes in impedance of the path that correspond to wet and dry states of the sensor. In response to detecting a change in impedance of the path, the sensing circuit signals an alert to a data processor that logs water exposure events in the device.

In another embodiment, a second water sensor that may be similar in structure to the first water sensor has its conductive path series coupled to that of the first water sensor and the sensing circuit. This enables the sensing circuit to respond to a change in impedance of any one of the conductive paths. For instance, each of the first and second sensors may be "normally shorted" until it has been immersed in water (for a duration and amount that is sufficient to dissolve enough of the bridge) so that an "open circuit" condition is created. The sensing circuit will be able to detect such a wet state when any one of the series coupled water sensors have been impacted in this manner.

In another embodiment, the carrier has several water sensors formed therein, where the conductive paths of these sensors are connected as a randomly accessible sensor array. Selection and sensing circuitry is coupled to the randomly accessible sensor array, to pass a current through any one of the respective conductive paths at a time, and then detect a change in impedance therein. The selection and sensing circuit in response to detecting the change in impedance (in any given active sensor element) will signal an alert to a data processor. The latter may then log a water exposure event in the device. The alert (and the resulting event) may also identify the respective conductive path or sensor element in which the impedance change was detected.

A method for manufacturing an electronic device having an integrated water sensor mechanism such as any of those described above involves depositing an amount of water-soluble conductive glue onto a pair of patterned conductor pieces formed in a component carrier of the device. A sufficient amount is deposited so as to fill an electrically insulating gap between the pair to form a conductive path that connects the pair. The glue may then be allowed to cure, before the path is formed. A sensing circuit is also installed on the carrier, coupled to the pair of patterned conductor pieces, which detects changes in impedance of the path caused by immersion of the path in water.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one.

FIG. 6 is a circuit diagram of an example implementation of the sensing circuitry.

FIG. 7 shows a series connection of multiple water sensors.

DETAILED DESCRIPTION

Several embodiments of the invention with reference to the appended drawings are now explained. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

Figure 1:
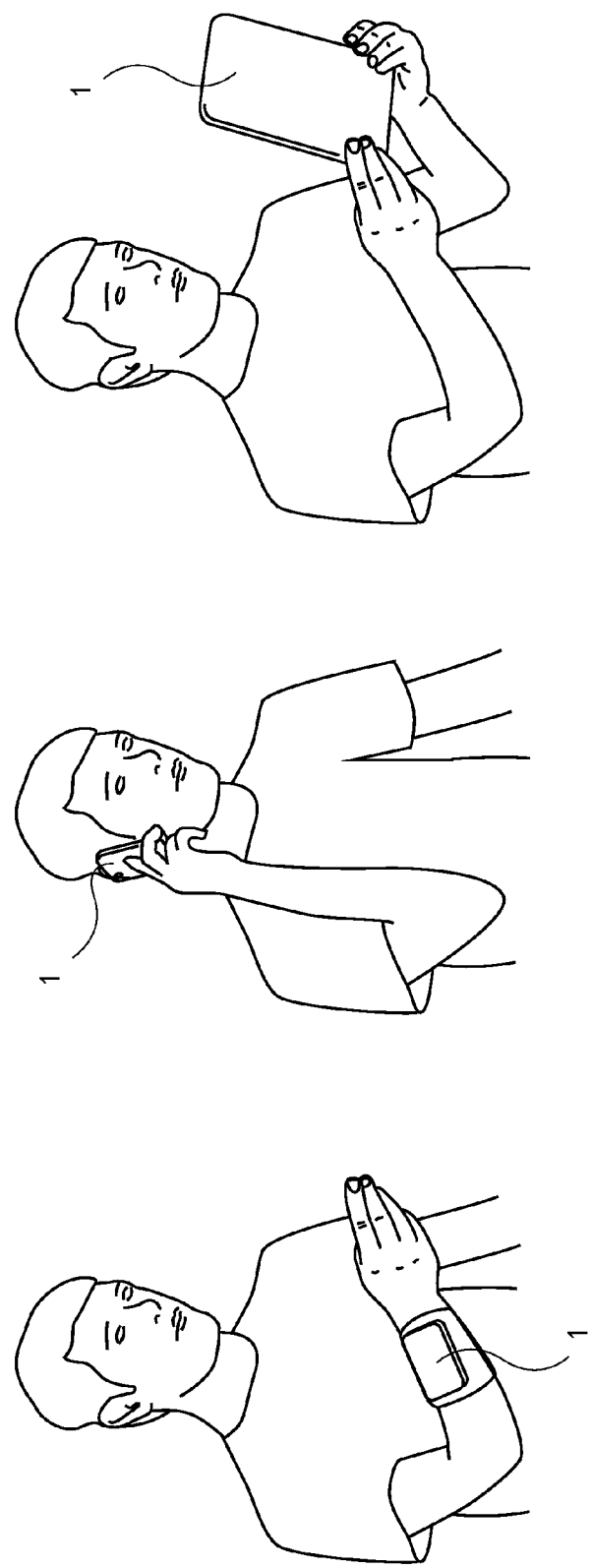
FIG. 1 shows several instances of an electronic device in which an embodiment of the invention may be implemented.

FIG. 1 shows a human user holding different types of a computing system being, in this example, a multi-function handheld mobile device also referred to here as a personal mobile device or a portable electronic device 1. In one instance, the mobile device 1 is a smart phone or a multi-function cellular phone with several features typically available in such modern devices, such as a touch screen interface, music and video file recording and playback, digital camera, video games, and wireless applications such as wireless internet telephony, cellular telephony, electronic calendar, web browser, and email. In another instance, the mobile device 1 may be a digital media player, such as an iPod Touch™ device depicted in FIG. 1 as being worn around the user's waist. In yet another instance, the mobile device 1 may be a larger, handheld tablet-like computer, such as an iPad™ device by Apple Inc. The mobile device 1 is more likely than, for example, a desktop computer, during its lifetime to be exposed to water in a manner that would damage its internal electronic components. The mobile device 1 could be immersed in water by being unintentionally dropped into a swimming pool or a large puddle, or by being used in non-recommended environments such as during a bath or exposed outside during a strong rain.

Figure 2:
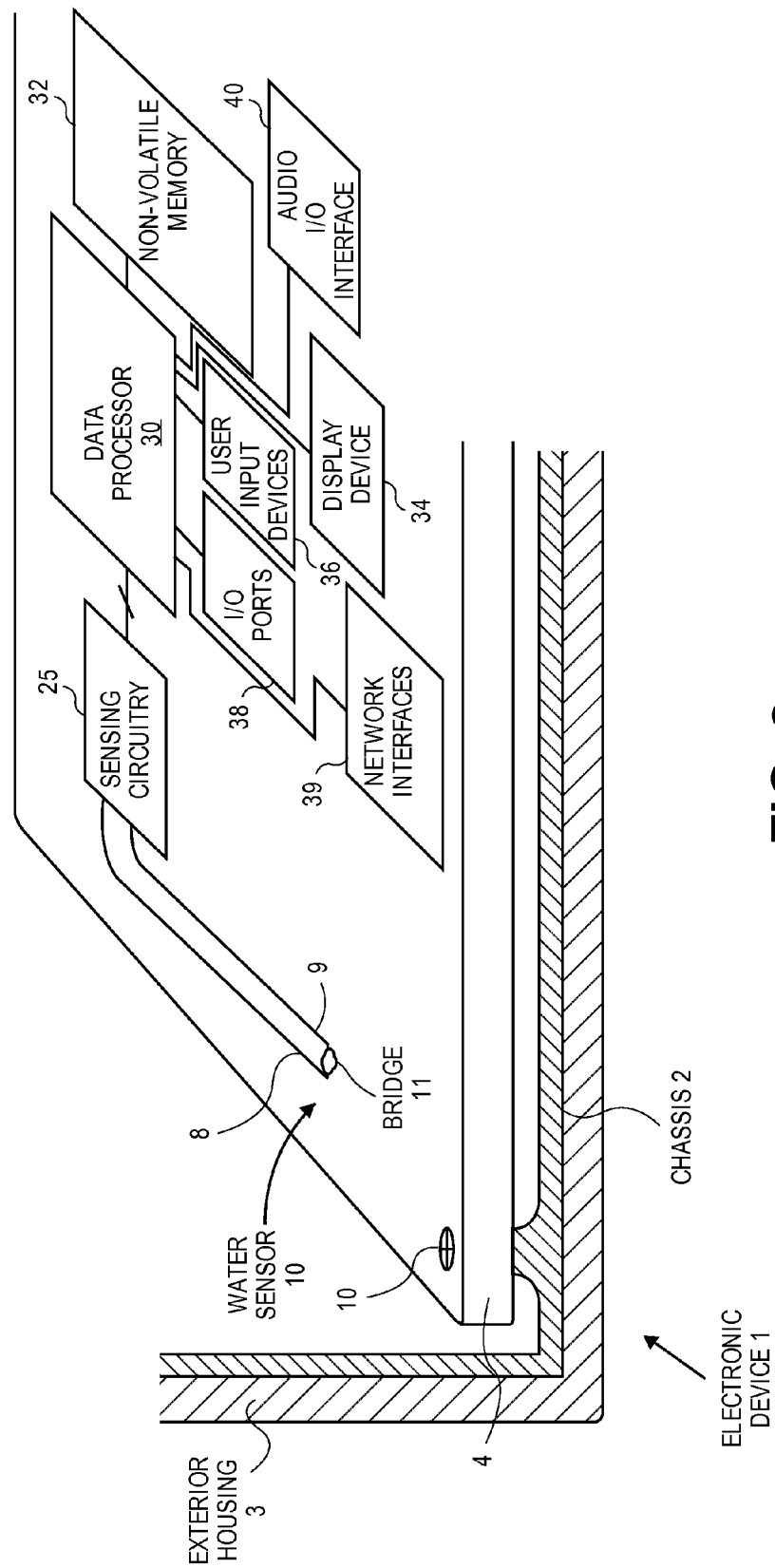
FIG. 2 is a combined elevation and block diagram view of a carrier inside an electronic device, showing a mechanism for detecting exposure to water.

FIG. 2 is a perspective or elevation view of the inside of the housing of such a device, showing a chassis 2 and a component carrier 4 having a water sensor mechanism in accordance with an embodiment of the invention. The carrier 4 may include a rigid printed wiring board (PWB) or printed circuit board (PCB), and/or it may include a flexible printed circuit. The carrier 4 may have two or more segments that are connected to each other by a flex circuit or connector, for example. The carrier 4 may be secured to the chassis using at least one fastener 10 that is installed in a hole or opening 6 in the carrier 4. The chassis 2 may be a separate metal frame or bracket inside an external housing 3 of the device, or it may be part of the external housing 3 itself (e.g., a plastic frame or support member having a chassis pad to which the fastener 10 may be affixed). The through hole 6 may be located inward of the boundary of the carrier 4 as shown in FIG. 2; alternatively, it may be right at the boundary or edge. The fastener 10 may be a screw, a nut and bolt combination, or other suitable alternative that can secure the carrier to the chassis through the hole 6.

Installed in the carrier 4 is a data processor 30 which may be any conventional programmable microprocessor-based circuitry that uses non-volatile memory 32 to perform various typical functions (e.g., general purpose computing, desktop computer applications, mobile applications including wireless telephony and wireless Internet access, and multimedia recording and playback, e.g. video and audio). These functions are performed using the following hardware components (also installed or wired into the carrier 4) that are typical of a computing system: I/O ports 38 (e.g., serial computer peripheral communications bus), user input devices 36 (e.g., keyboard, mouse, and touch sensitive panels), display device 34 (e.g., a liquid crystal display panel), audio I/O interface 40 (e.g., microphones and speakers), and network interfaces 39 (e.g., network interface controllers for Ethernet and wireless local area network protocols, and mobile telecommunications and cellular telecommunications transceiver circuitry).

The carrier 4 has formed therein a water sensor 10. The water sensor 10 is constituted by a first patterned conductor piece 8, which is formed in a metal layer of the component carrier 4. The first patterned conductor piece 8 may be a trace, a line, a pad, a ring, or a via that can be formed during the usual PCB fabrication process as part of a top metal layer, for instance, as shown. A bridge 11 being an amount of water-soluble conductive glue fills an electrically insulating gap between the first patterned conductor piece 8 and another conductor 9 in the carrier 4. This forms a conductive path between the patterned conductor piece 8 and the conductor 9. For example, the bridge 11 may be a measured amount of water-soluble conductive glue that has been deposited onto the conductors 8, 9 and then allowed to cure into a final shape and hardness, before the device 1 is ready to be sold. In one embodiment, the bridge 11 completes a conductive path between the first patterned conductor piece 8 and the another conductor 9, where this the path is coupled to the sensing circuitry 25 by at least one signal trace. The sensing circuitry 25 is also installed in the carrier 4 (although it need not be on the same segment of the carrier 4 as the water sensor 10). The sensing circuit 25 is to detect changes in impedance of the path, particularly when the bridge 11 has been immersed in a sufficient amount of water that has dissolved part or all of the conductive glue so as to change the impedance of the path.

When the sensing circuitry 25 has detected a change in impedance of the conductive path, it may in response signal a water exposure event alert to the data processor 30 in the electronic device 1. The data processor 30 in turn may evaluate and log such an event in non-volatile memory 32, by creating a data structure of the event that identifies the particular water sensor 10 (if there is more than one in the carrier 4) and perhaps the time and date of the event, and may then disable operations of the device 1. For instance, all operations of the device 1 may be disabled in response to receiving the event alert, except for a message that is displayed instructing the user to return the device to its manufacturer for service. Additional details regarding such higher layer consumer abuse management functions that may be performed by the data processor 30 are given in U.S. Patent Application Publication No. 2009/0195394, filed Feb. 1, 2008, entitled "Consumer Abuse Detection System and Method".

Figure 3A:
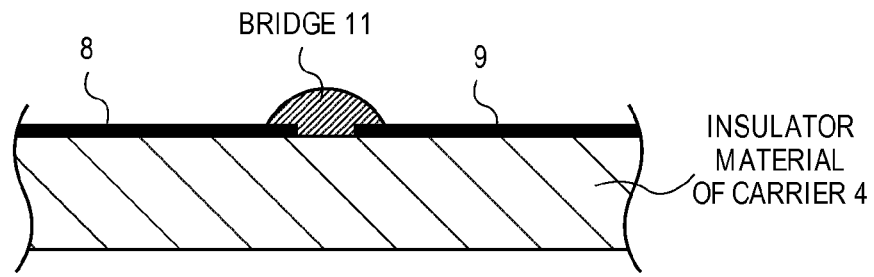
FIGS. 3A and 3B are cross-section views of one instance of a water sensor.
Figure 3B:
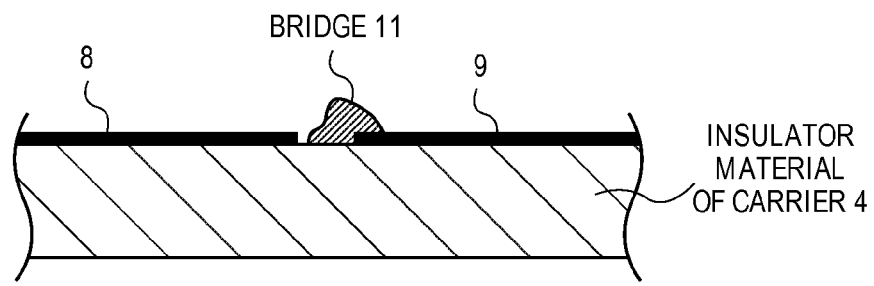

As seen in FIG. 3A, the conductive glue that constitutes the bridge 11 may be in contact with both the patterned conductor piece 8 and the other conductor 9, such that it is the only conductive path to speak of that connects the two, and any conductive path through the sensing circuitry 25 to which the patterned conductor piece 8 and conductor 9 are coupled may be negligible in comparison. In this embodiment, the sensor 10 is implemented entirely on a single face of the carrier 4 inside the electronic device housing 3, where each of the patterned conductor 8 and other conductor 9 is a separate or insulated circuit board trace. FIG. 3B shows a cross-section view of such a water sensor after a sufficient amount of water has washed away enough of the bridge 11, to result in a washed away bridge 11' that has exhibits higher impedance between the conductors 8, 9. This may be referred to as a "wet state" of the sensor. It should be understood that while the reference is to a "wet" state, the bridge 11' may have dried out at this point, leaving a partial bridge that is no longer in contact with at least one of the conductors 8, 9. In this example, enough of the bridge has been washed away such that there is essentially a true open circuit between the conductors 8,9. As seen in FIG. 3B, the washed bridge 11' has insufficient conductive material left to maintain the original conductive path between the patterned conductor piece 8 and the other conductor 9, such that the impedance now measured across the patterned conductor piece 8 and conductor 9 is substantially higher than was the case in the "dry state" of FIG. 3A.

Figure 4:
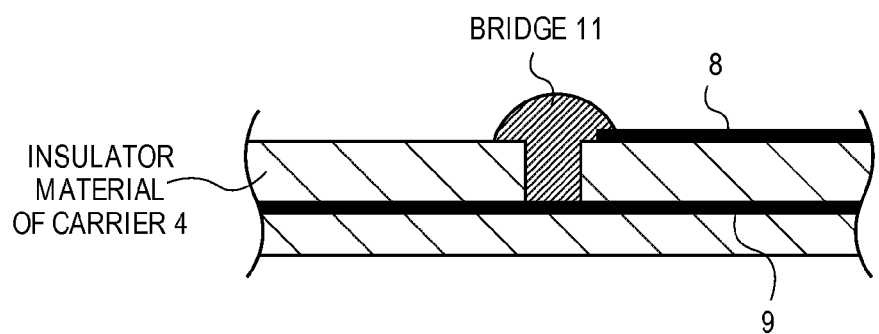
FIG. 4 is a cross-section view of another instance of the water sensor.

FIG. 4 depicts another instance of the water sensor 10, where the other conductor 9 is a second patterned conductor piece that is formed in a different metal layer than the first patterned conductor piece 8. In this example, the conductor 9 may be part of a ground plane of the carrier 4 in a buried metal layer of the carrier. A well is formed in the surface of the insulator layer, which is just below the top most metal layer. This well has been filled with a measured amount of the conductive glue that constitutes the bridge 11. The latter is in contact with a tip of the patterned conductor piece 8 and a portion of the ground plane (conductor 9) that is exposed at the bottom of the well, by virtue of filling the well. In one embodiment, the water-soluble conductive glue is of the kind that will be washed away or removed sufficiently, so that the bridge 11 will no longer be contacting the conductor 8 but may remain in contact with the conductor 9 in the wet state.

Figure 5:
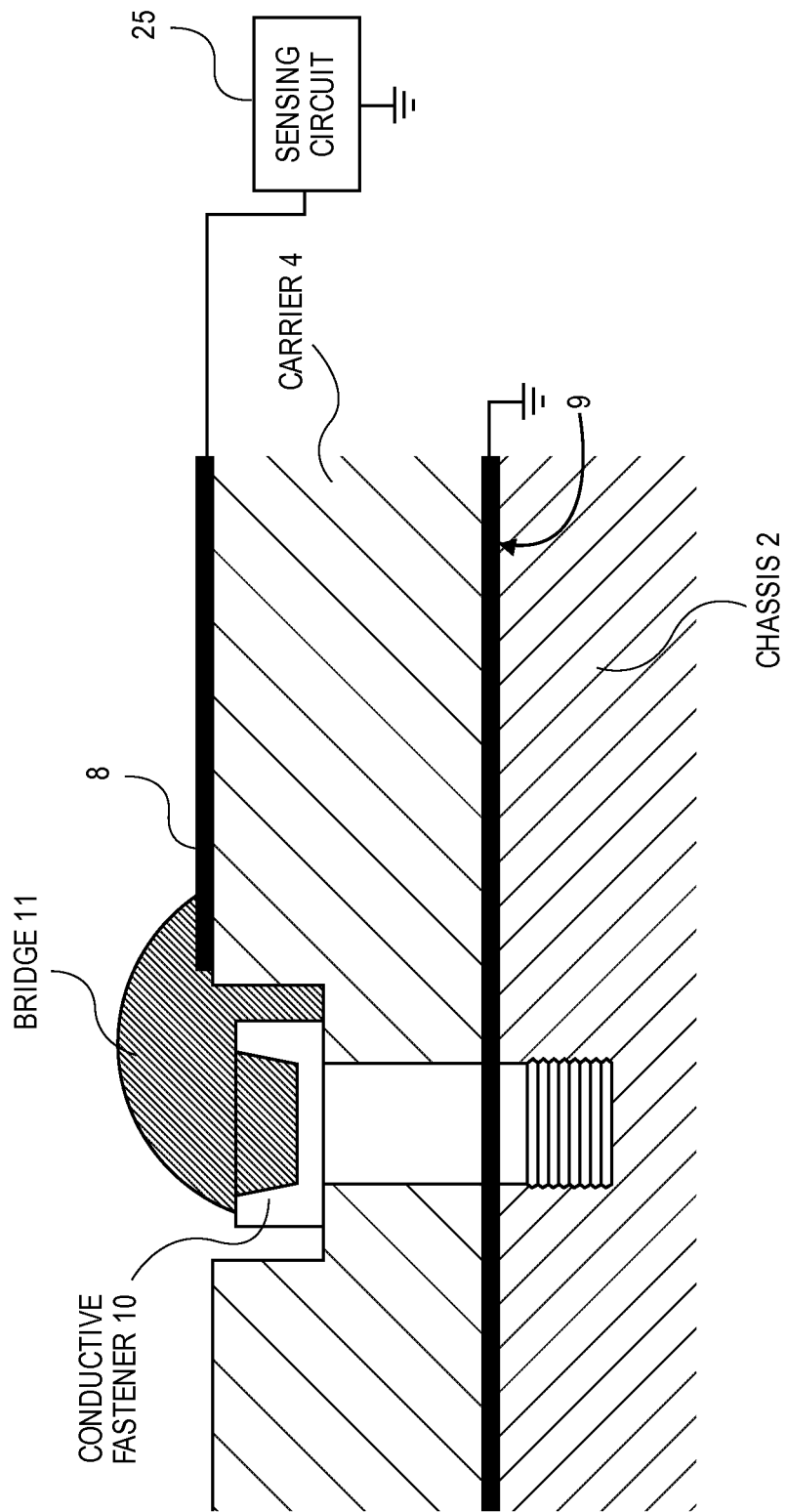
FIG. 5 is a cross-section view of yet another instance of the water sensor.

In yet another instance, depicted in FIG. 5, the water sensor 10 is formed by creating a bridge 11 that contacts a portion of the first conductor piece 8 on the one hand, and a conductive fastener 10 on the other. Thus, the other conductor 9 in this example is an exposed surface of the fastener 10 with which the conductive glue is in contact with as shown. The fastener 10 may be used to secure the carrier 4 through a hole therein, to the chassis 2 as shown. Alternatively, the fastener 10 may secure another segment of the carrier 4 or a connector (not shown) to the insulating portion of the carrier 4 depicted in the figure. In doing so, the fastener 10 may be in contact with a ground plane of the carrier 4; this is an example of a grounded water sensor 10. In that case, a single signal trace may be sufficient to couple the water sensor 10 to the sensing circuitry 25 since the latter can measure the change in impedance of the path created by the bridge 11 by virtue of being grounded itself. This arrangement is depicted in FIG. 5. Note also that in this example, the water sensor 10 is grounded by virtue of the metal fastener 10 being in contact with a grounded, metal portion of the chassis 2. Other ways of grounding the water sensor 10 are possible.

The water sensor 10 may be "permanent" in the sense that once a sufficient amount of water has come into contact with the bridge 11, the conductive glue may permanently change its resistance and therefore the conductive path impedance is changed permanently. This may be used to record the fact that the carrier 4 has been subjected to a sufficient amount of water (that would be likely to damage an electronic component inside the housing of the device 1). This could occur, for example, when the user inadvertently drops the device 1 into a swimming pool or a puddle, or exposes the device 1 to a large amount of water, such as during a strong rainstorm or use during a bath.

Two distinct conditions or states may be defined for the conductive path presented by the bridge 11. A dry impedance is defined as an impedance of the bridge when the bridge is relatively dry (from the time of manufacture of the device 1 up until the first time the bridge 11 is immersed in water). This "original" dry impedance may lie within a given resistance range that is defined by the conductivity of the water-soluble conductive glue as well as its amount and shape as used in the bridge 11. A different, wet impedance may be defined as referring to the bridge being sufficiently wet or washed away by a sufficient amount of water (see FIG. 3B for instance). The wet impedance may be higher than the dry impedance, e.g. a higher resistance to dc current. The water sensor may be such that once the bridge 11 has been immersed in water, the impedance of the conductive path presented by the bridge does not revert back to the original dry state even when the water has later evaporated from the bridge. In other words, the water in this case has essentially washed away or permanently altered some or all of the conductive glue. See, for instance, the wet state depicted in FIG. 3B.

Turning now to FIG. 6, a circuit schematic of an embodiment of the sensing circuitry 25 is shown. The sensing circuitry 25 receives as input a control signal (on/off) that controls a transistor switch 22 to activate the water sensor 10 by applying a dc voltage or current from a known current source 21. Note that while the water sensor 10 in this example is shown as being grounded, that is one of its conductors is directly connected to circuit ground, the sensor 10 need not be grounded but may instead be of the floating type (see, e.g. the sensors $S_1, S_2, \ldots S_{N-1}$ in FIG. 7 discussed below). An amplifier 23 is configured with some voltage gain, to measure the voltage developed across the sensor 10 (when the switch 22 has been turned on). A signal trace in this case directly connects another conductor of the water sensor 10 to a non-inverting input of the amplifier 23. A measure of the impedance of the sensor 10 is then taken, using a window detector 24 that includes a low comparator and a high comparator. The thresholds for these comparators may be set to an expected value or range, using respective digital to analog converters (DACs) 26. Decision logic at the output of the comparators 24 may be used to determine whether a measured voltage drop or impedance (that covers the conductive path) in the connected water sensor 10 is below, within, or above the predefined window. In essence, such a circuit compares the measured voltage drop or impedance (covering the conductive path of the water sensor 10) to the expected value or range, and may then record the measured voltage drop or impedance as either a dry impedance parameter or a wet impedance parameter of the conductive path. This is performed while a known dc current (using current source 21) is being passed through the conductive path. The output of the decision logic is a control signal referred to as water_exposure_alert, which is a signal that may be given to higher layer consumer abuse management functions that may be running in the data processor 30 (see FIG. 2).

The voltage range or window of the comparators 24 may be determined at the design or testing/manufacturing stage, where the water sensor 10 is tested while in its dry state. Actual tests or simulation of several activated water sensors may be performed, to select the voltage range or equivalent impedance range that is considered to be the original or dry state of the sensor 10. This window depends on the actual design of the water sensor 10, including the conductivity of the water-soluble conductive glue that constitutes the bridge 11. The window may be determined based on experimental analysis of a sample of the water sensor 10 in both the original dry state and in several different wet states. Statistical data may be taken from several such samples of the water sensor 10 and several instances of the wet states, to select a best fit window that defines the difference between the original dry state and a wet state. This defined window may then be stored in non-volatile memory 32 (see FIG. 2) of each high volume manufacture (HVM) or "production run" specimen of the device 1, such that the data processor 30 in the specimen, while running the appropriate software, can access this defined window from the memory 32 and program the DACs 26 accordingly, to initialize the threshold of the window detector 24 for operation. As an alternative, the window threshold may be hard-wired at the time of manufacture and assembly of the component carrier 4 for each specimen.

It should be noted that part of the functionality of the sensing circuitry 25 may be implemented in the programmed data processor 30. For example, the output of the amplifier 23 may be digitized and then read by the processor 30, where the latter then makes the measurement or comparison of this digitized value to a digital threshold value that defines the boundary between the original dry state and a wet state of the sensor 10. In other words, the comparison with the expected value may be performed by the data processor 30 (e.g., an applications processor or a power management unit controller).

Note that the above described window determination process may also be used to help select the amount or type of conductive glue that constitutes the bridge 11 so that, for instance, the resistance of the bridge 11 falls within a relatively narrow window.

Still referring to FIG. 6, the current source 21 may be programmable with several discrete dc current levels (e.g., 100 µA, 1 mA, and 2.5 mA). This would allow the data processor 30 to further customize the sensing circuitry 25 for a particular device 1, having a particular water sensor 10. As to the power supply (Vcc), this may be obtained from a battery in the device 1, or it may be another "always-on" power source rail. A protection diode may be included in series between the power source rail and the transistor switch 22. Also, the gain of the amplifier 23 may be programmable (under command of the data processor 30), in order to support different types of water sensors. It should be noted also that while the window detector 24 is shown as a pair of comparators, an alternative may be to use a single comparator for a less precise or broader definition of the dry and wet states. For instance, a single comparator may be used with a single threshold voltage, so that the dry state is defined as any voltage at the output of the amplifier 23 that is below that threshold, and the wet state is defined as any voltage across the water sensor 10 that is above that threshold.

Turning now to FIG. 7, a series connection of multiple water sensors 10 is shown. Each of these sensors $S_1, S_2, \ldots S_N$ may be deemed to have a low resistance in its original or dry state (referred to here generically as shorted or "normally shorted"), until it has been immersed in water, thereby causing the bridge 11 associated with each sensor to be washed away or otherwise altered. When any one of these sensors is affected in this manner, a high resistance condition (or generically referred to here as "open circuit") is created in the series branch. This is, of course, detected by the sensing circuitry 25 as an increased total voltage (measured across the entire group of sensors). In other words, the sensing circuitry 25 can respond to a change in impedance of any one of the conductive paths of the sensors $S_1, S_2, \ldots S_N$. A single water exposure alert signal may then be asserted by the sensing circuitry 25 in response, which signal is then delivered to the data processor 30. Higher layer consumer abuse management functions running in the data processor 30 may then log a water exposure event in response to this signal being asserted.

Figure 8:
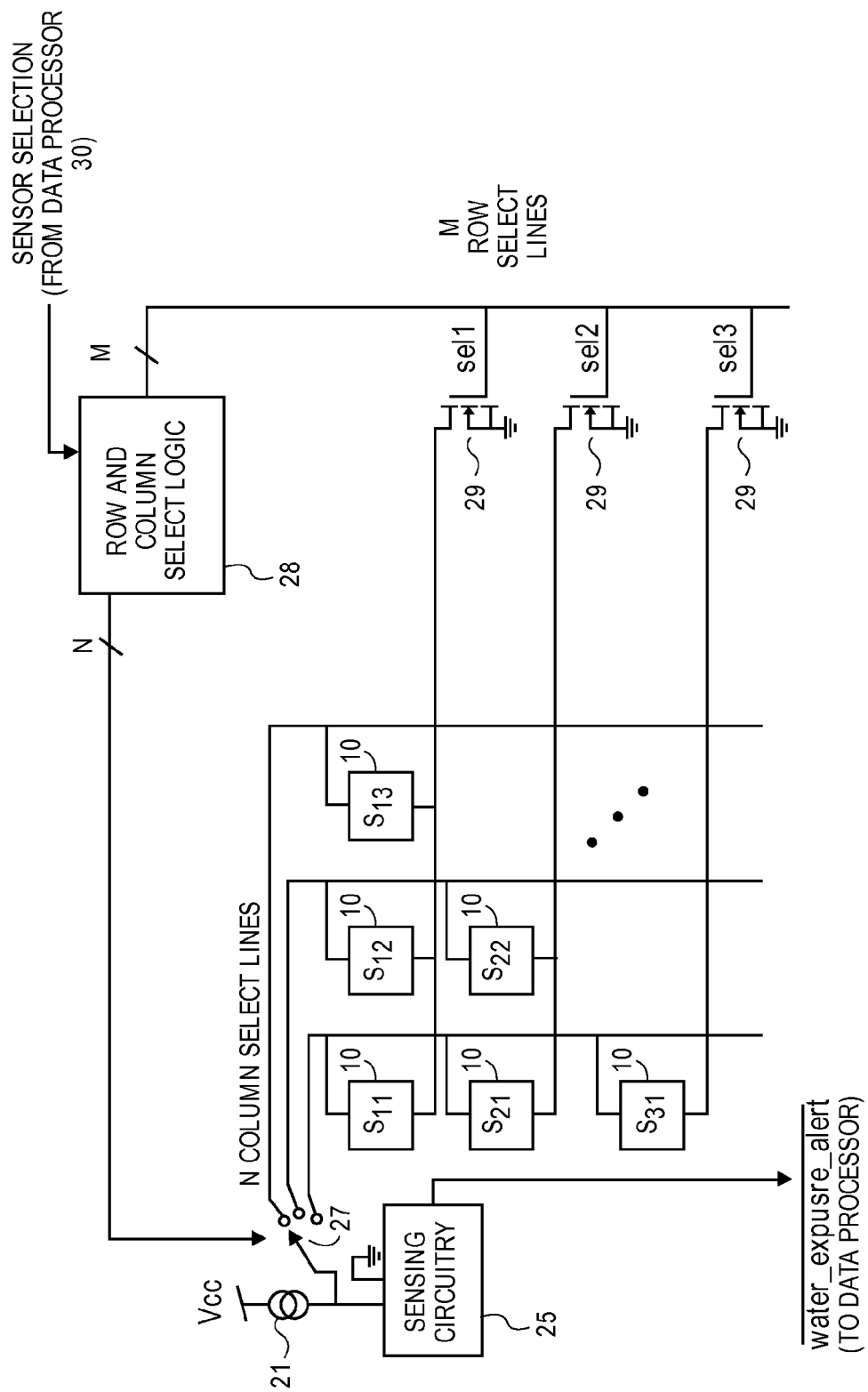
FIG. 8 shows an array of water sensors coupled to selection logic and sensing circuitry.

Turning now to FIG. 8, another multi-sensor arrangement is shown that is also effective in reducing pin count. Here, an array of water sensors $S_{11}, S_{12}, \ldots S_{NN}$ are shown, where there are M×N sensors in the array. This array of matrix arrangement is also referred to as a scanned sensor embodiment, where individual column select and row select lines are connected to the array of sensors, to yield a randomly accessible sensor array. In addition to providing lower pin count, such an arrangement also allows isolation of any desired individual sensor $S_{ij}$, to pinpoint a fault or water exposure event, in addition to achieving a reduction in power consumption since only a single sensor need be turned on or activated at any given moment. For instance, to activate sensor $S_{22}$, only row select line 2 and only column select line 2 would be activated, thereby enabling the current source 21 to force a current through only that sensor. Note that for convenience, all of the sensors may be replicates of each other, although this is not necessary. The sensing circuitry 25 is connected to a particular column select line through a switch or multiplexer 27 as shown, thereby enabling it to detect the state of any one of the sensors as commanded by the row and column select logic 28. A single sensor can be selected by having only the transistor switch 29 of that row turned on. The row and column select logic 28 decodes a sensor selection received from the data processor 30, into the appropriate column and row select lines to be activated. Note that in this embodiment, the row select lines are relatively high impedance lines that are connected to the gates or control electrodes of respective transistor switches 29, whereas the column select lines would be switched to the current source 21 for activating or driving a given sensor. A designation of "column" and "row" is only used to distinguish between those two types of select lines and is not otherwise intended to limit the arrangement of the randomly accessible sensor array.

Figure 9:
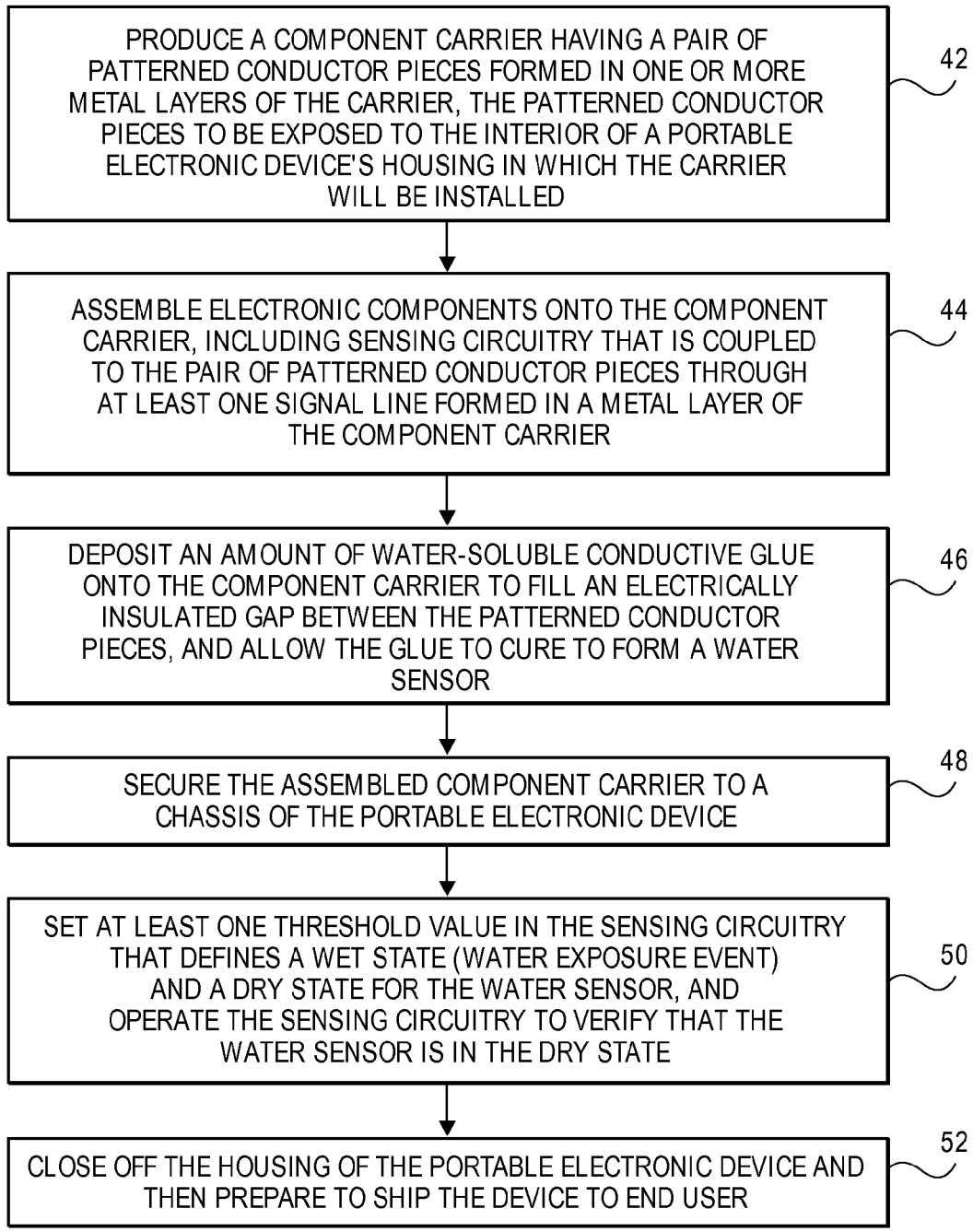
FIG. 9 is a flow diagram of a manufacturing and production test process for a water sensor mechanism in an electronic device.

Referring now to FIG. 9, a flow diagram of a manufacturing and production test process for a water sensor mechanism is described. Operation begins with a component carrier being produced that has a pair of patterned conductor pieces formed in one or more layers of the carrier (operation 42). Note that as an alternative, just one patterned conductor piece may be formed, while the other conductor used for the water sensor may be a fastener that may be installed in the carrier at a later point. The patterned conductor piece is to be exposed to the interior of a portable electronic device's housing in which the carrier will be installed.

Operation continues with electronic components being assembled onto the carrier, which includes sensing circuitry that is coupled to the pair of patterned conductor pieces through at least one signal line formed in a metal layer of the carrier (operation 44). These electronic components may include an applications processor package, a non-volatile memory package or module, and other electronic components found in a mobile device that are typically soldered to their respective metal pads on a surface of the component carrier.

The manufacturing process also includes the following operation, namely that an amount of water-soluble conductive glue is deposited onto the component carrier, to fill an electrically insulated gap between the patterned conductor pieces (operation 46). This may be a measured amount of a water-soluble conductive glue fluid that conforms to the shape of the conductive patterned pieces with which it will be in contact with (as well as the insulating portion of the carrier that insulates the two patterned pieces). The conductive glue may then be allowed to cure and harden to form a water sensor. It should be noted that while this operation is described after the electronic component assembly of operation 44, operation 46 may actually precede the assembly of any of the electronic components of operation 44. For example, if the water-soluble conductive glue can withstand the relatively high temperatures presented during a surface mount component solder process (e.g., a solder reflow process), then the conductive glue may be deposited onto the carrier before the solder reflow process. The assembled component carrier may then be secured to a chassis of the portable electronic device (operation 48).

Operation continues with at least one threshold value being set (or, alternatively hard-wired) in the sensing circuitry that defines a boundary between a wet state and a dry state of the sensor (block 50). The water sensor may be operated and tested by measuring or evaluating the output of the sensing circuitry 25 to which it is coupled (see FIGS. 2 and 6). The dry state of the water sensor may be verified as falling within a predefined window, for example, and then recorded within a non-volatile memory of the device. The assembled component carrier may now be deemed to have passed this aspect of the production test, such that the process may continue with operation 52.

Note that as an alternative, all or most of the electronic components may be assembled onto the carrier, and then this populated carrier may be secured to the chassis, prior to the depositing of the water-soluble conductive glue in operation 46. In other words, operation 46 may come after all of the conventional electronic component solder reflow operations and carrier installation procedures have been completed, but prior to the external housing of the portable electronic device being closed off (operation 52). Following this operation, the portable electronic device is ready to be prepared and shipped to an end user.

Figure 10:
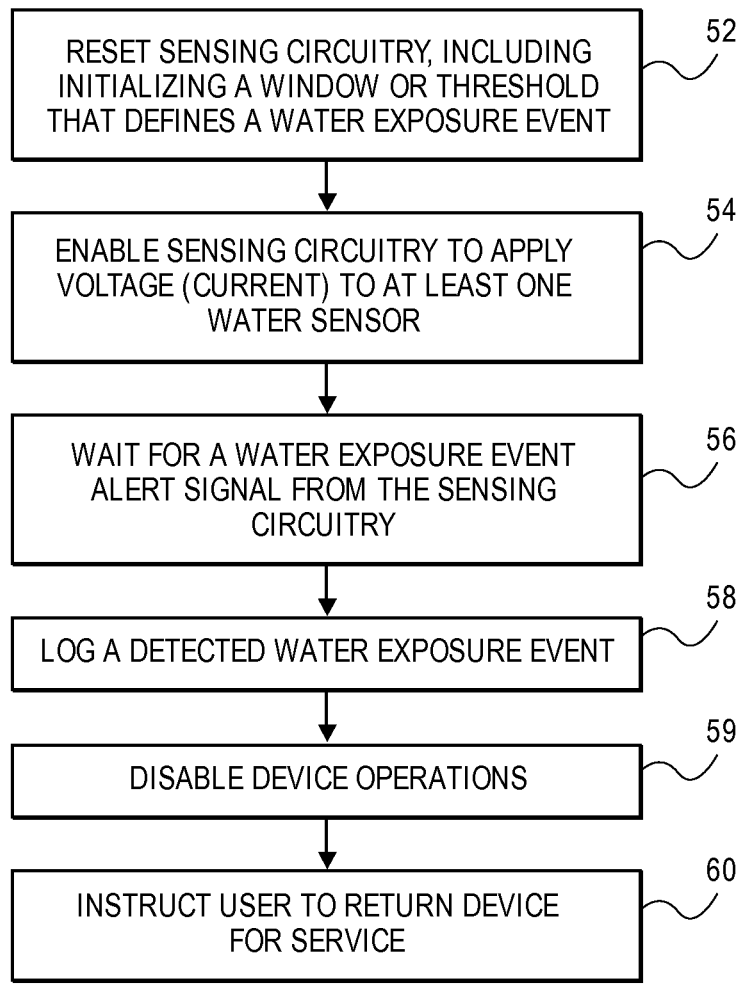
FIG. 10 is a flow diagram of a water exposure event process in an electronic device.

Turning now to FIG. 10, a flow diagram of a water exposure event process running in an electronic device is shown. The process may begin with operation 53 in which the sensing circuitry (e.g., see FIG. 6) is reset, including a window or threshold being initialized that defines a water exposure event. Note that as an alternative, the window or threshold that defines the water exposure event may have been hard-wired into the sensing circuitry 25. Next, the sensing circuitry 25 is enabled or activated, to apply current to at least one water sensor that is coupled to it (operation 54). This may be done by the data processor 30 asserting the on/off signal to the sensing circuitry 25—see FIG. 6. Next, the data processor waits for a water exposure event alert signal from the sensing circuitry (operation 56). It should be noted that this reference to the data processor "waiting" encompasses both the situation where the processor may be polling the sensing circuitry, as well as when it is being interrupted by the alert signal. Once the alert is received, a detected water exposure event is logged (operation 58). This may include identifying the particular sensor for which the alter has been received (e.g., using the randomly accessible sensor array embodiment of FIG. 8), and storing this identification together with a time and date stamp associated with the alert. The logged event may be stored in non-volatile memory inside the electronic device. Next, certain functionality or operations of the electronic device may be disabled (operation 59) and an instruction may be displayed or given to the end user of the device to return it for service (operation 60). Once the device has been returned to the manufacturer, the logged event may be read from memory and the water sensor may be inspected to confirm that the device was, in fact, exposed to a potentially damaging amount of water.

Figure 11:
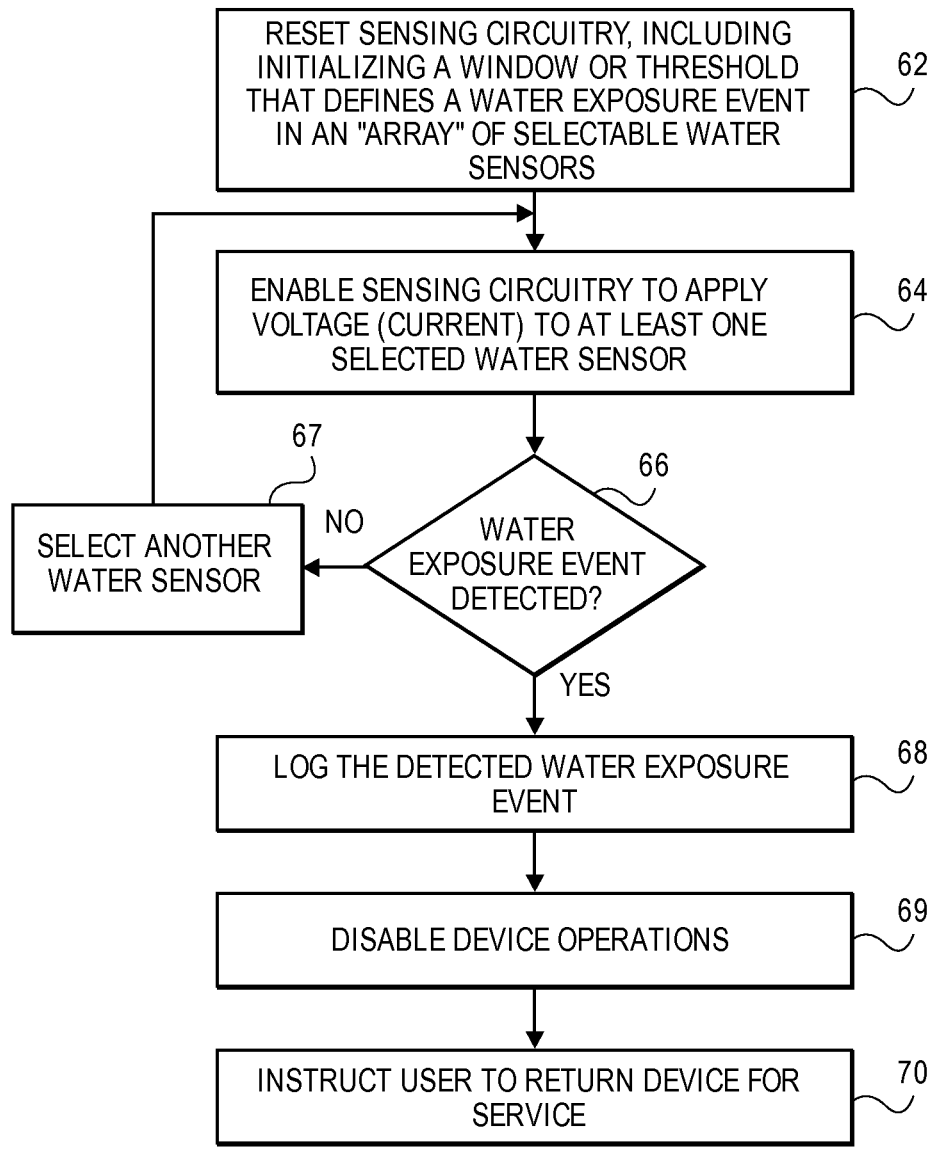
FIG. 11 is a flow diagram of another process for water exposure events, involving a selectable sensor array.

FIG. 11 is a flow diagram of a water exposure event process in an electronic device, this time involving a selectable randomly accessible sensor array such as the one depicted in FIG. 8. Operation begins with block 62 in which the sensing circuitry 25 is reset, including optionally initializing one or more thresholds that define water exposure events in the array of selectable water sensors. Note that each water sensor may be associated with a different window or threshold, provided that the sensing circuitry 25 is capable of being reconfigured or programmed for each such different window or threshold. Operation then continues with block 64 in which the sensing circuitry is enabled to apply current to at least one selected water sensor. This may be achieved by sending a sensor selection command from the data processor 30 to the row and column select logic 28 depicted in FIG. 8. The latter in response decodes the requested selection into the appropriate or respective pair of column and row select lines that are then activated or asserted, to activate the respective water sensor. This causes the sensing circuitry 25 to be connected to only a particular sensor in the array. If a water exposure event is then detected at that point (block 66), then the sensing circuitry asserts its alert signal, in response to which the data processor logs a water exposure event that is associated with the selected sensor (block 68). If, however, no water exposure event is detected by the sensing circuitry 25, then the data processor, recognizing this, selects another water sensor (block 67). This is, of course, achieved by sending another sensor selection signal command to the row and column select logic 28. The array may thus be scanned in this manner until a water exposure event is detected and logged in block 68. Thereafter, device functionality or operations may be disabled in response to a detected water exposure event (block 69) and the end user may be instructed to return the device for service (in block 70).

In accordance with another embodiment of the invention, a discrete, solder reflowable water sensor component, for example, similar to a discrete resistor in form factor, has the same changeable impedance properties as the carrier-based water sensor 10 described above. In other words, the component contains a bridge made of water-soluble conductive glue that forms a conductive path that connects a pair of solder terminals of the component. The impedance of this path (as measured across the solder terminals) changes into a fairly well-defined impedance range in response to the bridge coming into contact with a sufficient amount of water. Such a component would be soldered onto a component carrier during a solder reflow type component installation process. In contrast, the carrier-based water sensor 10 may be produced by applying or depositing the water-soluble conductive glue at final assembly, after the high temperature, surface mount automated process of solder reflow process has been completed. This discrete component sensor may be otherwise operated in the same manner as the carrier-based water sensor 10, i.e. by being coupled to the sensing circuitry 25 as depicted in FIGS. 6-8 and operated as per the water exposure event processing in FIGS. 10-11.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, although only mobile devices are depicted in FIG. 1, an embodiment of the invention may alternatively be implemented as a water sensor mechanism in a non-mobile device such as a desktop computer or a television set-top box. The description is thus to be regarded as illustrative instead of limiting.

What is claimed is:

1. An electronic device comprising:
    a component carrier having formed therein a first water sensor, the first water sensor having a first patterned conductor piece formed in a metal layer of the component carrier and a bridge being an amount of water-soluble conductive glue filling an electrically insulating gap between the first patterned conductor piece and another conductor in the component carrier to form a conductive path between the first patterned conductor piece and the another conductor, wherein the conductive path dissolves and an open circuit forms between the first patterned conductor piece and the another conductor in response to exposure of the bridge to water; and
    a sensing circuit coupled to the first patterned conductor piece and the another conductor to detect changes in impedance of the path.

2. The electronic device of claim 1 wherein the component carrier is a rigid printed wiring board (PWB), and the another conductor is a further patterned conductor piece formed in a metal layer of the PWB.

3. The electronic device of claim 1 wherein the component carrier is a flex substrate circuit, and the another conductor is a further patterned conductor piece formed in a metal layer of the flex circuit.

4. The electronic device of claim 1 wherein the another conductor is a metal fastener attached to the component carrier.

5. The electronic device of claim 1 wherein the another conductor is a second patterned conductor piece formed in the same outermost metal layer of the carrier as the first patterned conductor piece.

6. The electronic device of claim 1 wherein the conductive path has an original dry state impedance when the bridge is dry and a different, wet state impedance when the bridge is wet, wherein the wet state impedance is greater than the dry state impedance.

7. The electronic device of claim 6 wherein the first water sensor is such that once the bridge has been immersed in water, the impedance of the conductive path does not re-form when the water has later evaporated from the bridge.

8. The electronic device of claim 6 wherein the sensing circuit to compare a measured voltage drop or impedance covering the conductive path, to an expected value, and record the measured voltage drop or impedance as a dry state impedance parameter of the conductive path.

9. The electronic device of claim 1 wherein the sensing circuit is to, in response to detecting a change in impedance of the path, signal an alert to a data processor that logs water exposure events in the electronic device.

10. The electronic device of claim 1 further comprising:
    a second water sensor having a first patterned conductor piece formed in the carrier and a bridge being an amount of water soluble conductive glue filling an electrically insulating gap between the first patterned conductor piece and another conductor to form a conductive path, wherein the conductive paths of the first and second water sensors are coupled in series with the sensing circuit so that the sensing circuit responds to a change in impedance of any one of the conductive paths.

11. The electronic device of claim 1 wherein the conductive path has a first impedance when the bridge has not been exposed to water, and a second impedance when the bridge has been exposed to water, the second impedance greater than the first impedance.

12. A method for manufacturing an electronic device, comprising:
    depositing an amount of water-soluble conductive glue onto a component carrier of the device to fill an electrically insulating gap between a first patterned conductor piece and another conductor in the carrier to form a conductive bridge that connects the first patterned conductor piece and the another conductor, wherein the conductive bridge dissolves and an open circuit forms between the first patterned conductor piece and the another conductor in response to exposure of the bridge to water, thereby forming a water sensor; and
    installing a sensing circuit on the carrier coupled to the first patterned conductor piece and the another conductor, wherein the sensing circuit is to detect a change in impedance of the conductive bridge caused by immersion of the bridge in water.

13. The method of claim 12 further comprising:
    setting a threshold value for the sensing circuit that defines a water exposure event for the water sensor, wherein the sensing circuitry is to apply a current to the water sensor and compare an output value of the water sensor to the threshold value to determine whether to signal a water exposure event.

14. An electronic device comprising:
    a component carrier having a plurality of water sensors formed therein, each water sensor having a pair of patterned conductor pieces formed in the carrier and a bridge being an amount of water-soluble conductive glue filling an electrically insulating gap between the pair to form a respective conductive path that connects the pair, wherein the respective conductive path dissolves and an open circuit forms between the pair in response to exposure of the bridge to water, the respective conductive paths being connected as a randomly accessible sensor array; and
    a selection and sensing circuit coupled to the randomly accessible sensor array, to pass a current through any one of the respective conductive paths at a time and then detect a change in impedance therein, the selection and sensing circuit to, in response to detecting the change in impedance, signal an alert to a data processor that evaluates and logs water exposure events in the device.

15. The electronic device of claim 14 wherein the selection and sensing circuit is to receive a sensor selection from a data processor and decode the selection into respective column and row select lines of the array and then activate the respective column and row select lines to pass a current through a respective one of the water sensors only.

16. The electronic device of claim 14 wherein the respective conductive path has an original dry state impedance when the bridge is dry and a different, wet state impedance when the bridge is wet, wherein the wet state impedance is greater than the dry state impedance.

17. The electronic device of claim 16 wherein the water sensor is such that once the bridge has been immersed in water, the impedance of the conductive path does not re-form when the water has later evaporated from the bridge.

18. The electronic device of claim 14 wherein the respective conductive path has a first impedance when the bridge has not been exposed to water, and a second impedance when the bridge has been exposed to water, the second impedance greater than the first impedance.

19. An electronic device comprising:

a component carrier having a plurality of components installed thereon including (1) a discrete water sensor component, the discrete water sensor component having a pair of terminals and a bridge being an amount of water-soluble conductive glue filling an electrically insulating gap between the pair to form a conductive path that connects the pair, wherein the respective conductive path dissolves and an open circuit forms between the pair in response to exposure of the bridge to water, and (2) a sensing circuit coupled to the terminals of the discrete water sensor component, to detect a change in impedance of the path and in response signal a water exposure alert.

20. The electronic device of claim 19 wherein the conductive path has a first impedance when the bridge has not been exposed to water, and a second impedance when the bridge has been exposed to water, the second impedance greater than the first impedance.

* * * * *